United States Patent [19]

Christian et al.

[11] Patent Number: 5,314,071

[45] Date of Patent: May 24, 1994

[54] GLASS SORTER

[75] Inventors: Donald J. Christian; Chin-Hu Feng, both of Fremont; Jerry L. McComas, Sunnyvale; Andrew K. Chang, Los Altos Hills, all of Calif.

[73] Assignee: FMC Corporation, Chicago, Ill.

[21] Appl. No.: 988,556

[22] Filed: Dec. 10, 1992

[51] Int. Cl.$^5$ .................. B03B 1/00; B07C 5/342
[52] U.S. Cl. .................. 209/4; 209/581; 209/587; 209/639; 241/14; 241/24; 241/68
[58] Field of Search ............ 209/580, 581, 582, 588, 209/638, 639, 930, 3, 4, 587; 241/24, 68, DIG. 38, 14, 102

[56] References Cited

U.S. PATENT DOCUMENTS

| | | | |
|---|---|---|---|
| 3,802,558 | 4/1974 | Rhys | 209/580 X |
| 3,897,330 | 7/1975 | Rhys | 209/580 X |
| 4,379,525 | 4/1983 | Nowicki et al. | 241/24 X |
| 4,657,144 | 4/1987 | Martin et al. | 209/639 X |
| 4,765,489 | 8/1988 | Satake | 209/587 X |
| 5,148,923 | 9/1992 | Fraenkel et al. | 209/580 X |
| 5,148,993 | 9/1992 | Kashiwagi | 241/24 |
| 5,215,772 | 6/1993 | Roth | 209/587 X |

FOREIGN PATENT DOCUMENTS

0183340  10/1984  Japan .................. 209/580

Primary Examiner—D. Glenn Dayoan
Assistant Examiner—Tuan N. Nguyen
Attorney, Agent, or Firm—Michael Lee; R. C. Kamp; R. B. Megley

[57] ABSTRACT

The invention provides a method and apparatus for purification and color sortation of waste glass, a glass beneficiation process and apparatus. The invention crushes the glass into pieces less than 3 inches in size, delables the glass, and then sorts the glass according to the light transmissive properties of the glass utilizing an array of lamps electrically connected to a control module.

17 Claims, 8 Drawing Sheets

FIG_1

FIG_2

FIG_6

FIG_11
TWO-COLOR HIGH PURITY SORTING SYSTEM

FIG_7

FIG_8A

FIG_8B

FIG_9

FIG_10

FIG_12

GLASS SORTER

BACKGROUND OF THE INVENTION

The invention provides a method and apparatus for purification and color sortation of waste glass, a glass beneficiation process and apparatus.

DESCRIPTION OF THE PREFERRED EMBODIMENT

Figure 1:
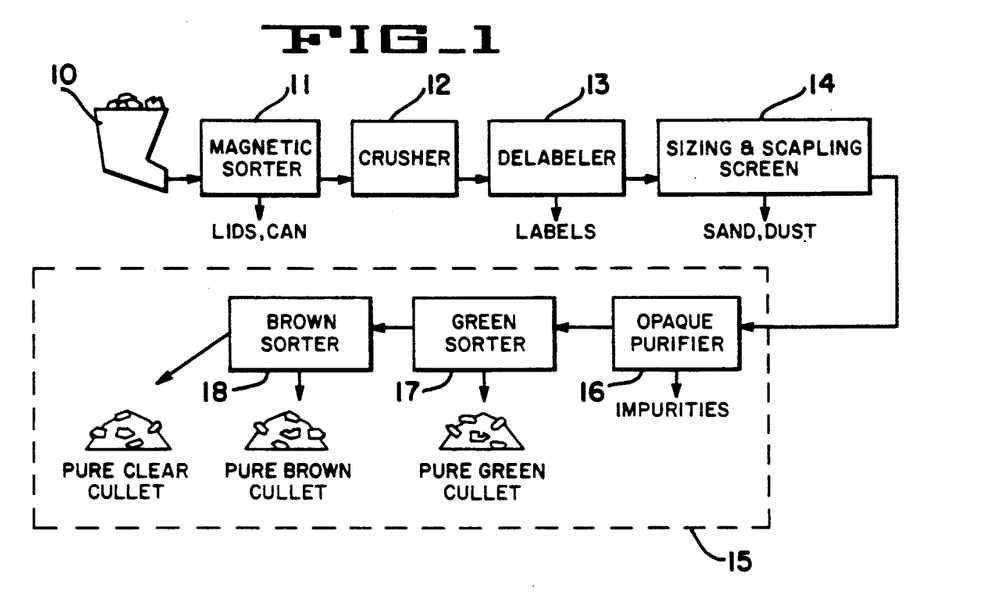
FIG. 1 is a schematic view of an apparatus for processing broken and whole glass containers.

In FIG. 1 a loader/feeder 10 provides a continuous load or discrete loads of whole and broken glass containers to a magnetic sorter 11. The magnetic sorter 11 uses magnets to remove magnetic objects such as cans and lids from the load. The load then is passed to a crusher 12, which crushes broken and whole glass containers into pieces of glass. The load then is passed to a delabler 13, which removes pieces of labels from the pieces of glass in the load. The load is then passed through a sizing and scalping screen 14, which separates particles in the load by size. Particles that are too small, less than ¼ inch, such as dust or sand are removed from the load as waste. Particles that are too large, greater than 3 inches, are sent back to the crusher 12. The remaining load is then passed to a glass sorter 15, which comprises an opaque purifier (sorter) 16, a green sorter 17, and a brown sorter 18.

Figure 2:
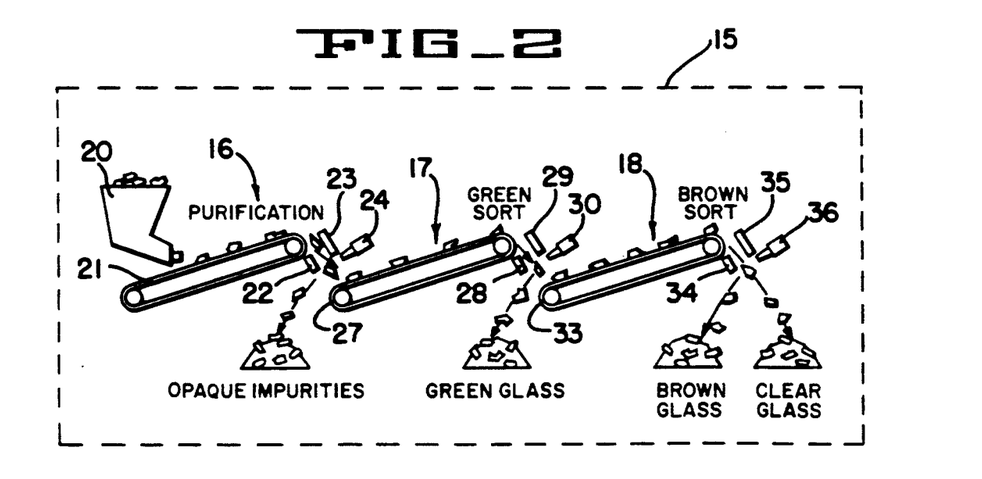
FIG. 2 is a more detailed schematic diagram of the glass sorter shown in FIG. 1.

FIG. 2 is a more detail schematic diagram of the glass sorter 15. A vibratory feeder 20 is adjacent to the opaque purifier 16. The opaque sorter 16 comprises a first conveyor 21 with a first end and a second end wherein the first end of the first conveyor 21 is adjacent to the vibratory feeder 20, a first lamp array 22 adjacent to the second end of the first conveyor 21 a first sensor array 23 adjacent to the first lamp array 23, and a first ejector array 24 adjacent to the first sensor array 23. The green sorter 17 comprises a second conveyor 27 with a first end and a second end, wherein the first end of the second conveyor 27 is adjacent to the first ejector array 24, a second lamp array 28 adjacent to a second end of the second conveyor 27 a second sensor array 29 adjacent to the second lamp array 28, and a second ejector array 30 adjacent to the second sensor array 29. The brown sorter 18 comprises a third conveyor 33 with a first end and a second end, wherein the first end of the third conveyor 33 is adjacent to the second ejector array 30, a third lamp array 34 adjacent to a second end of the third conveyor 33 a third sensor array 35 adjacent to the third lamp array 34, and a third ejector array 36 adjacent to the third sensor array 35.

Figure 3:
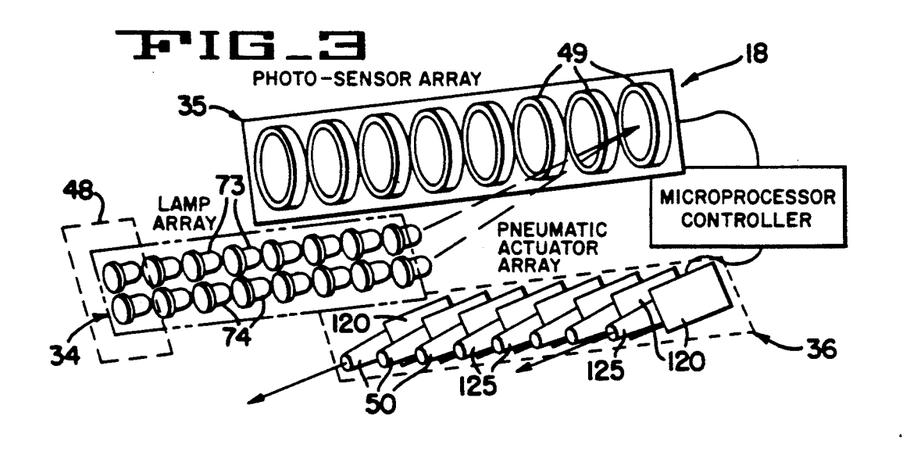
FIG. 3 is a more detailed view of a sorter and control system used in the embodiment in FIG. 1.

FIG. 3 illustrates a more detailed view of part of the brown sorter 18. In the preferred embodiment, each lamp 48 of the lamp array 34 comprises a green light emitting means 73 and a red light emitting means 74. In the preferred embodiment the green light emitting means 73 and the red light emitting means 74 are HBG5066X green and red LED's sold by Stanley Sales of Irvine, California. Each sensor 49 in the third sensor array 35 are SD-076-12-22-001 photo sensors sold by Silicon Detector Corporation of Camarillo, Calif. Each actuator 50 in the third ejector array comprises a 35A-EAEDDFJaKE-M599 pneumatic solenoid 120 manufactured by Mac Valves and a model 354 air jet guide 125 manufactured by Adams. The green sorter 17 and the opaque sorter 16 may be made of the same component parts.

Figure 4:
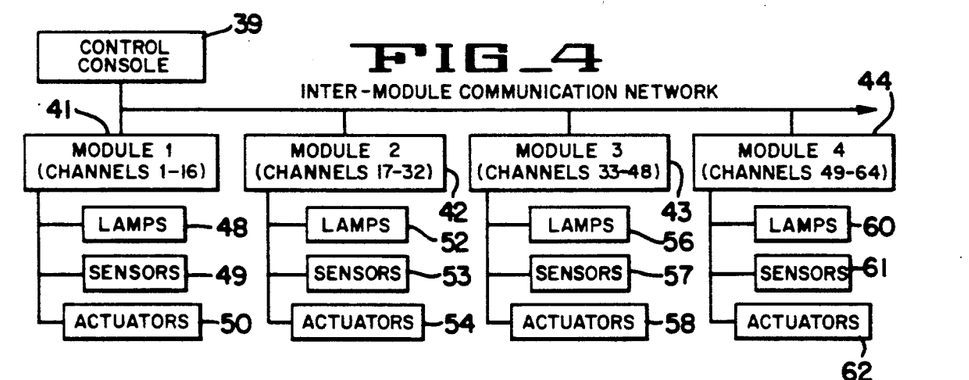
FIG. 4 is a schematic illustration of part of the electronic controls of a glass sorter.

FIG. 4 is a schematic illustration of the electronic controls of the brown sorter 18. In the preferred embodiment a control console 39 is electrically connected to four control modules 41, 42, 43 and 44. The first control module 41 is electrically connected to a first bank of lamps 48, a first bank of sensors 49, and a first bank of actuators 50. Each bank has sixteen items, therefore the first bank of lamps 48 has sixteen lamps. The second control module 42 is electrically connected to a second bank of lamps 52, a second bank of sensors 53, and a second bank of actuators 54. The third control module 43 is electrically connected to a third bank of lamps 56, a third bank of sensors 57, and a third bank of actuators 58. The fourth control module 44 is electrically connected to a fourth bank of lamps 60, a fourth bank of sensors 6 1, and a fourth bank of actuators 62. In this embodiment, the first, second, third, and forth bank of lamps 48, 52, 56 and 60 form the third lamp array 34, the first, second, third, and fourth banks of sensors 49, 53, 57, and 61 form the third sensor array 35, and the first, second, third, and fourth actuators 50, 54, 58 and 62 form the third ejector array 36. Each lamp, sensor, and ejector represents a channel. Each channel represents a strip 0.25 inches wide. Since the brown sorter 18 has sixty four channels, the brown sorter 18 handles a sorting conveyor 16 inches wide. The opaque and green sorters 16, 17 have electronic controls identical to the brown sorter 18.

Figure 5:
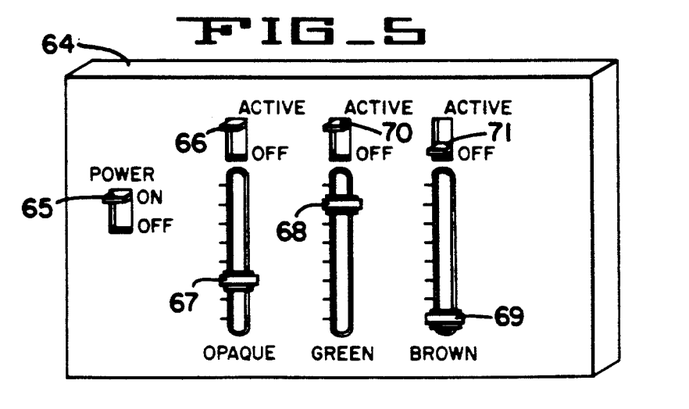
FIG. 5 illustrates a control panel to a control console used in a glass sorter.

FIG. 5 illustrates the control panel 64 to the control console 39. The control panel comprises a power switch 65, an opaque actuator control 66, a green actuator control 70, and a brown actuator control 71, an opaque sensitivity control 67, a green sensitivity control 68, and a brown sensitivity control 69. The control panels of the control consoles of the opaque and green sorters 16, 17 are identical to the control panel 64 of the brown sorter 18.

In operation, a load of glass is introduced by the loader feeder 10 to the magnetic sorter 11. The magnetic sorter 11, uses magnets to remove magnetic material such as lids and cans from the load. The load is then transferred to the crusher 12, which crushes the glass in the load. The load is then transferred to the delabeler 13, which removes labels from the glass. The load is then transferred to the sizing and scalping screen, which removes pieces that are too small, returns pieces that are too large to the crusher 12, and feeds the remaining load to the first end of the first conveyor 21 of the opaque purifier 16. The first conveyor 21 conveys the glass to a position above and directs the glass between the first lamp array 22 and the first sensor array 23. The direction by the conveyor between the first lamp and sensor arrays 22, 23 is the falling of the glass along a trajectory. The first lamp array 22 directs light through the glass to the first sensor array 23, the information is processed as described below, and the first ejector array 24 ejects opaque materials from the path of flow. Material not ejected fall on the first end of the second conveyor 27, which directs the glass to a point above and then between the second lamp array 28 and the second sensor array 29. The second lamp array 28 directs light through the glass to the second sensor array 29 and the second ejector array deflects green glass out of the flow, while the remaining glass falls onto the first end of the third conveyor 33, which directs the glass to a point above and then between the third lamp array 34 and the third sensor array 35. The third lamp array 34 directs light through the glass to the third sensor array 35 and the third ejector array deflects brown glass out of the flow, while the remaining glass, which is clear glass falls into a clear glass area.

Figure 6:
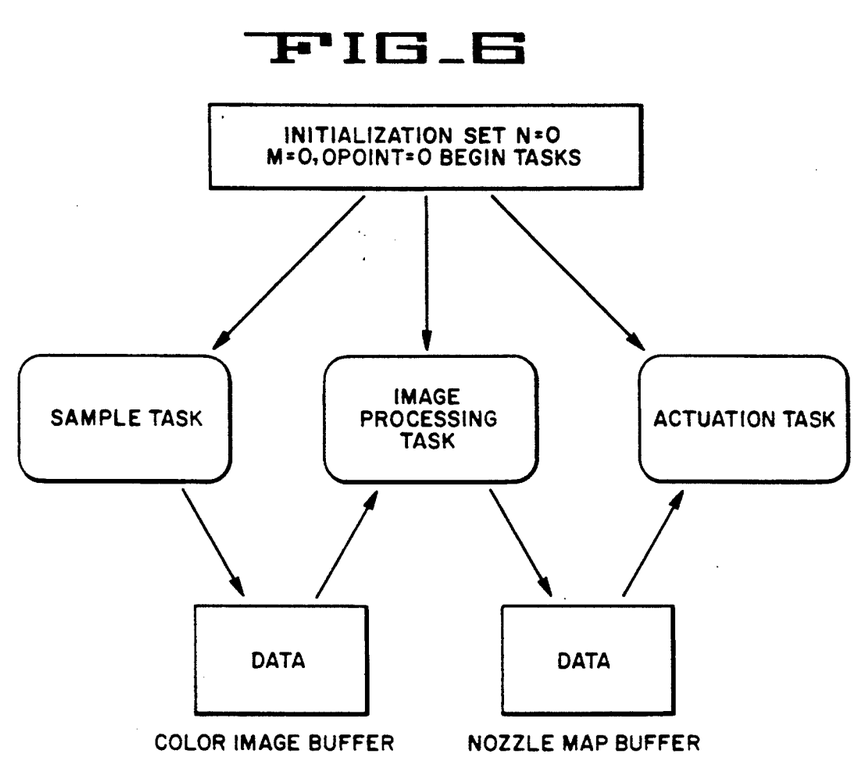
FIG. 6 is a data flow diagram of a glass sorter.
Figure 7:
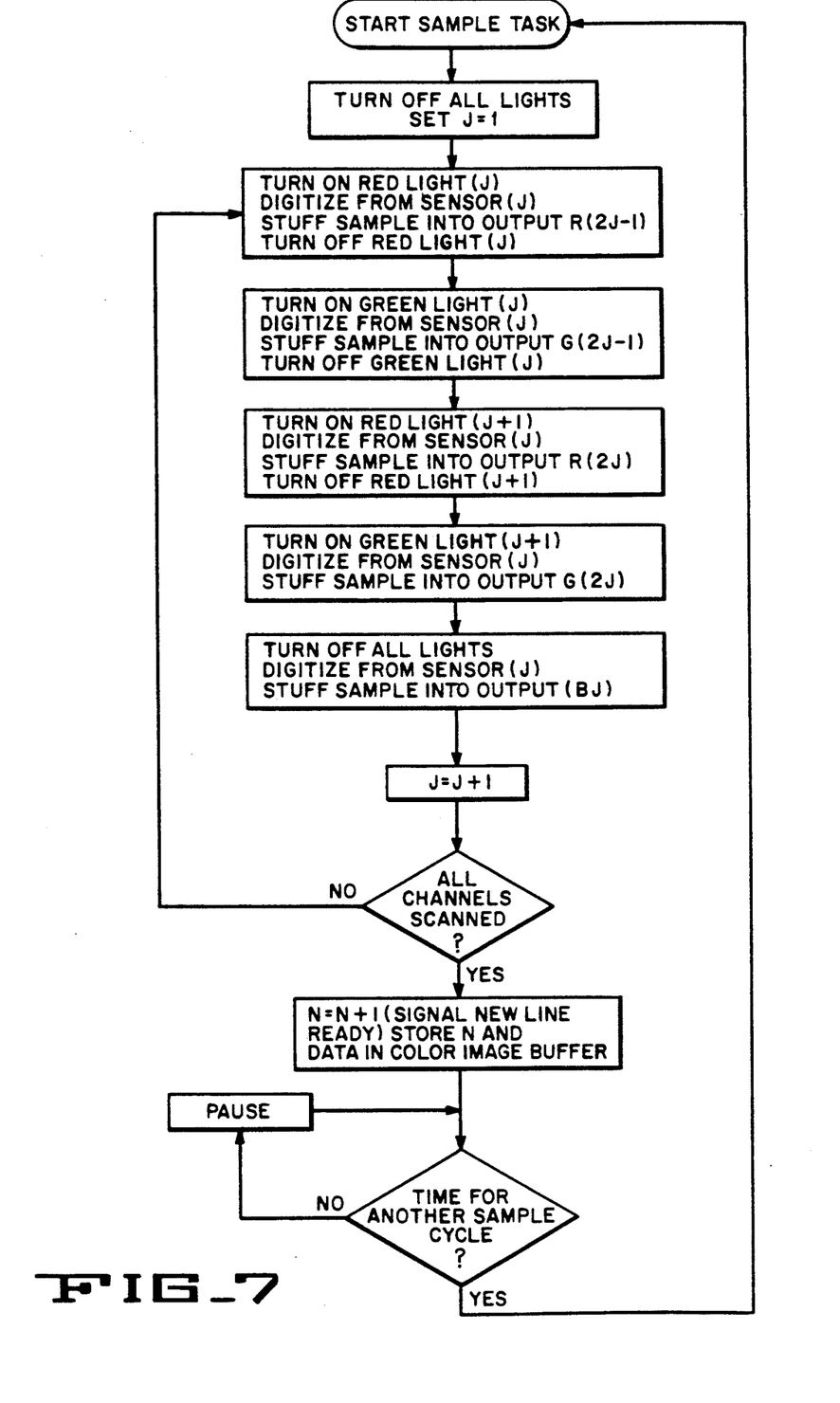
FIG. 7 is a flow chart of a sample task.
Figure 8A:
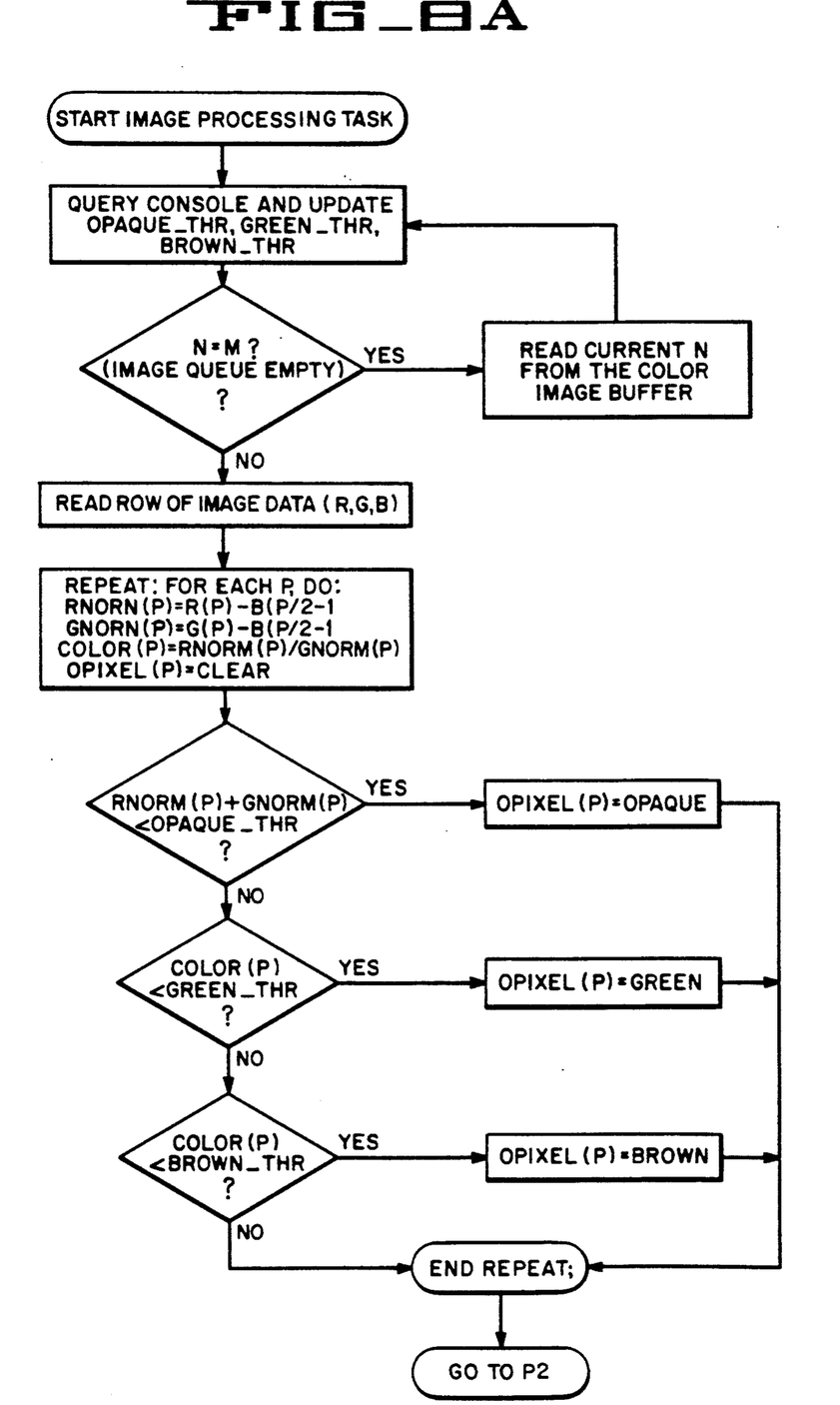
FIGS. 8A and 8B are a flow chart of the image processing task.

The computational load to process the signals detected by the sensor to control the actuators is uneven and "bursty". Because of the uneven, bursty computational demands of the algorithm, the software is structured as a group of three intercommunicating tasks the sample task, the actuation task and the image processing task. The tasks are shown in the data flow diagram in FIG. 6. Each task is scheduled for execution on a priority demand basis, with the background (Image Processing) task given lowest priority. This allows tasks to be asynchronously decoupled and thereby insures that CPU cycles will be available when required for time-critical operations. The priority assigned in the preferred embodiment is first priority given to the sample task, second priority given to the actuation task and third priority given to the image processing task. FIGS. 7, 8A, are flow charts of the sample and imaging cycles which work together. First an initialization procedure sets N=O, M=O, and Opoint=O. N is the counter used by the Sample Task. M is the counter used by the Image Processing Task, and Opoint is the counter used by the Actuation Task. After the initialization procedure is completed the tasks begin.

The sample task comprises of the following procedure, which is illustrated by the flow chart of FIG. 7 and which cycles through on a timed schedule. The shorter the intervals between Sample Task cycles means the better the spatial resolution. The maximum frequency is limited by the speed of the processor. Each Sample Task cycle goes through the following procedure.

For each detector J in the array,

1. Turn OFF all lights, and set J=1.
2. Turn on red LED emitter(J) and take a digital sample from photo-sensor(J). Store the sample as R(2J-1). Turn red LED emitter(J) off.
3. Turn on green LED emitter(J) and take a digital sample from photo-sensor(J). Store the sample as G(2J-1). Turn green LED emitter(J) off.
4. Turn on red LED emitter(J+1) and take a digital sample from photo-sensor(J). Store the sample as R(2J). Turn red LED emitter(J+1) off.
5. Turn on green LED emitter(J+1) and take a digital sample from photo-sensor(J). Store the sample as G(2J). Turn green LED emitter(J+1) off.
6. Turn off all LEDs and take a digital sample from photo-sensor(J). Store the sample as B(J).
7. Increment J=J+1
8. Repeat steps 2 to 7, until all photo-sensors have been fully scanned.
9. When all photo-sensors have been fully scanned, N (which is initialized to zero by the image processing task when the system is started) is incremented and a signal and the data are sent to the image processing task. The sample task is then suspended until a set interval has passed, and then the sample task is repeated.

Figure 9:
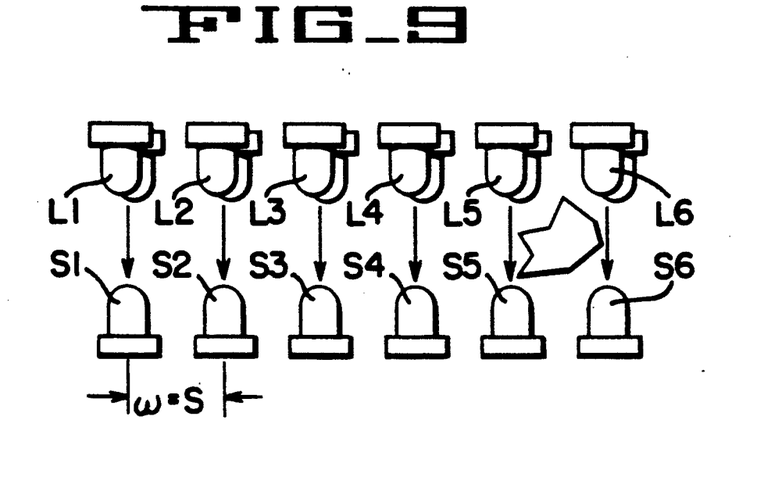
FIG. 9 illustrates an undithered glass sorter.
Figure 10:
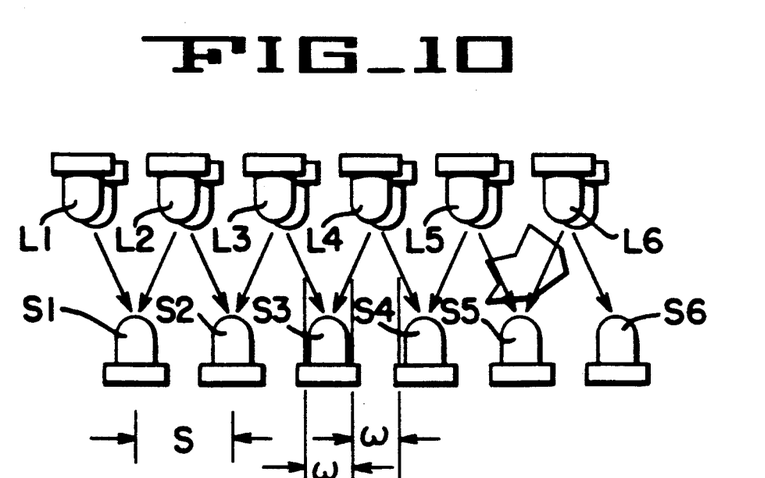
FIG. 10 illustrates a dithered glass sorter.

FIG. 9, illustrates an undithered apparatus, where data for a photo-sensor S(J) is gathered from a lamp L(J) of red and green diodes. The spacing between adjacent lights and adjacent sensors is labeled S. The Nyquist theorem imposes a theoretical limit on the minimum particle size which can not slip between sampling beams undetected. With an undithered scan, this size is approximately equal to S (the sensor spacing). FIG. 10 illustrates a dithered apparatus where data for a photo-sensor S(J) is gathered from two lamps L(J) and L(J+1) of red and green diodes. The dithered scan improves the resolution by a factor of 2 so that minimum particle size is about S/2, (shown as w). This improves sorter performance for small particles. The above sample sequence uses a dithered scan using inputs from red and green lights (J) and (J+1) as inputs to photo-sensor (J).

Figure 8B:
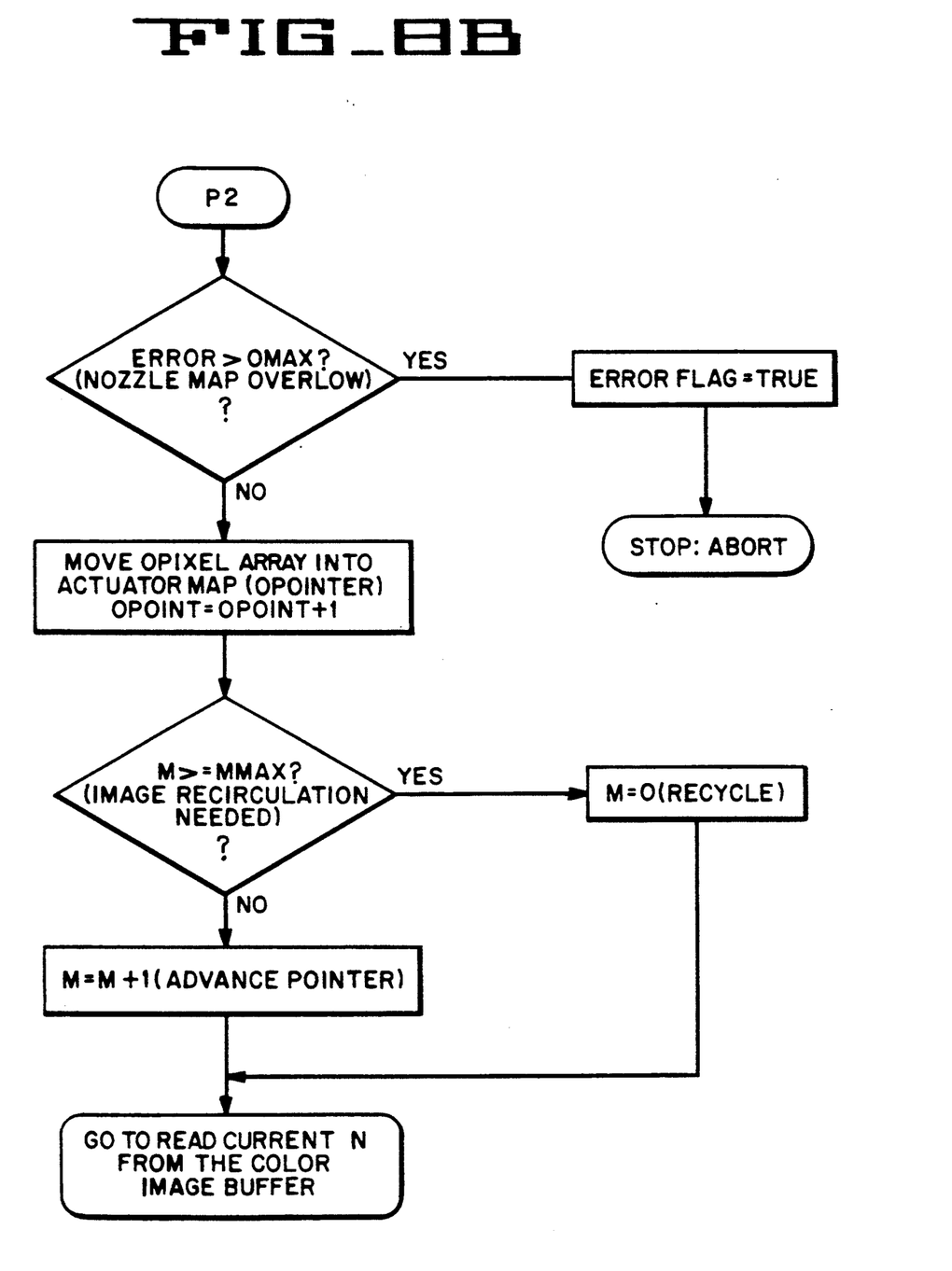

The Image Processing task performs a imaging operation for each multi-dimensional pixel thereby reducing the overall volume of the data. The Image Processing task is performed when the processor is available (not performing a sample task cycle) and when data is available in the Color Image Buffer from the Sample Task. This is indicated when N>M. FIGS. 8A and 8B are a flow chart of the process used to perform the imaging operation.

The image processing task consists of the following logical steps:

1. The color image circular output pointer is compared with the input pointer (N=M?). If they are equal, then the task suspends itself for a short period of time and restarts itself beginning at this step. As soon as the pointers are no longer equal, then the Image Task is allowed to proceed.
2. At occasional intervals (embedded in the task suspension procedure in the preferred embodiment), the control console is queried for the status of the threshold selection controls. These status values are used to update the variables Opaque_Thr, Green_Thr, and Brown_Thr.
3. A row of sensor readings are input from the sensor array, based on the position of the circular output pointer.
4. A single "color pixel" is developed which consists of a red sensor reading, a green sensor reading, and a black sensor reading. The three readings can be viewed as three dimensions, with the pixel being a 3-dimensional vector in the space. All three readings were taken from the same sensor, within a very short time of one another (typically a few microseconds). These readings are extracted from the Color Image as R(N), G(N), and B(N/2+1).
5. The color pixel is normalized through the following transformations:

$$Rnorm(N) = R(N) - B(N/2+1)$$

$$Gnorm(N) = G(N) - B(N/2+1)$$

at the left of each row (382 ... 401) is a time-stamp, and is expressed in milliseconds as measured from the start of the test. Individual elements which have values greater than 1.2 are underlined.

| | | | | | | | | | | | | | | | |
|---|---|---|---|---|---|---|---|---|---|---|---|---|---|---|---|
| 382 | 1.05 | 1.00 | 1.00 | 0.99 | 1.06 | 1.02 | 0.96 | 1.02 | 0.99 | 1.02 | 1.00 | 1.01 | 1.02 | 1.00 | 0.98 | 1.02 |
| 383 | 1.05 | 1.00 | 1.00 | 0.99 | 1.06 | 1.00 | 1.15 | 1.00 | 0.98 | 1.02 | 1.00 | 1.01 | 1.02 | 1.01 | 0.99 | 1.01 |
| 384 | 1.05 | 1.00 | 0.99 | 0.99 | 1.04 | 0.99 | _2.10_ | 1.02 | 0.99 | 1.01 | 1.00 | 1.01 | 1.01 | 1.00 | 0.99 | 1.01 |
| 385 | 1.05 | 1.00 | 1.00 | 0.99 | 1.04 | _1.78_ | 0.90 | 1.16 | 0.98 | 1.02 | 1.00 | 1.01 | 1.01 | 1.00 | 0.98 | 1.01 |
| 386 | 1.05 | 1.00 | 1.00 | 0.99 | _1.35_ | _5.49_ | 1.16 | 1.15 | 0.99 | 1.02 | 1.00 | 1.01 | 1.01 | 1.00 | 0.99 | 1.02 |
| 387 | 1.05 | 1.00 | 1.00 | 0.99 | 1.10 | 1.00 | _1.24_ | _1.31_ | 0.99 | 1.02 | 1.00 | 1.01 | 1.01 | 1.01 | 0.99 | 1.02 |
| 388 | 1.06 | 1.00 | 1.00 | 0.99 | 1.10 | _1.62_ | _1.27_ | _1.57_ | 0.99 | 1.02 | 1.00 | 1.01 | 1.01 | 1.00 | 0.99 | 1.02 |
| 389 | 1.05 | 1.00 | 1.00 | 0.99 | _1.21_ | _1.70_ | _1.37_ | _1.54_ | 0.99 | 1.02 | 1.00 | 1.01 | 1.02 | 1.01 | 0.99 | 1.02 |
| 390 | 1.05 | 0.99 | 1.00 | 0.99 | _1.24_ | _1.70_ | _1.58_ | _1.26_ | 0.98 | 1.02 | 1.00 | 1.00 | 1.01 | 1.01 | 0.99 | 1.02 |
| 391 | 1.05 | 1.00 | 1.00 | 0.99 | _1.33_ | _1.83_ | _1.57_ | _1.57_ | 1.05 | 1.02 | 0.99 | 1.01 | 1.01 | 1.00 | 0.99 | 1.02 |
| 392 | 1.05 | 1.00 | 1.00 | 0.99 | 0.99 | _2.05_ | _1.52_ | _1.44_ | _1.30_ | 1.02 | 1.00 | 1.00 | 1.01 | 1.00 | 0.99 | 1.01 |
| 393 | 1.05 | 1.00 | 1.00 | 0.99 | 0.64 | _2.24_ | _1.69_ | _1.61_ | _1.94_ | 1.02 | 1.00 | 1.00 | 1.02 | 1.01 | 0.99 | 1.02 |
| 394 | 1.05 | 1.00 | 1.00 | 0.99 | 0.92 | _1.24_ | _1.62_ | _2.26_ | _4.79_ | 1.02 | 1.00 | 1.01 | 1.01 | 1.01 | 0.99 | 1.02 |
| 395 | 1.05 | 0.99 | 1.00 | 0.99 | 1.06 | 0.59 | _2.02_ | _1.28_ | _1.41_ | 1.02 | 1.00 | 1.01 | 1.02 | 1.01 | 0.99 | 1.02 |
| 396 | 1.05 | 0.99 | 1.00 | 0.99 | 1.05 | 0.76 | _1.63_ | _1.89_ | 1.13 | 1.01 | 1.00 | 1.01 | 1.01 | 1.00 | 0.99 | 1.02 |
| 397 | 1.04 | 1.00 | 0.99 | 0.99 | 1.06 | 0.94 | 0.48 | _1.30_ | _2.39_ | 1.07 | 1.00 | 1.01 | 1.01 | 1.01 | 0.99 | 1.02 |
| 398 | 1.05 | 1.00 | 1.00 | 0.99 | 1.05 | 1.02 | 0.51 | _1.64_ | _1.87_ | _1.40_ | 1.00 | 1.01 | 1.01 | 1.00 | 0.99 | 1.02 |
| 399 | 1.05 | 1.00 | 1.00 | 0.99 | 1.05 | 1.02 | 0.87 | _1.66_ | _1.42_ | _1.54_ | 1.00 | 1.00 | 1.01 | 1.00 | 0.99 | 1.02 |
| 400 | 1.05 | 1.00 | 1.00 | 0.99 | 1.06 | 1.02 | 0.99 | 0.55 | _1.96_ | 0.86 | 1.00 | 1.01 | 1.02 | 1.00 | 0.99 | 1.02 |
| 401 | 1.05 | 1.00 | 0.99 | 0.99 | 1.06 | 1.02 | 0.99 | 0.69 | 0.44 | 0.71 | 1.00 | 1.01 | 1.02 | 1.01 | 0.99 | 1.01 |

6. The opacity is measured as if (Rnorm(N)+Gnorm(N)<Opaque_Thr) then Label_Pixel_Opaque
7. The Color is measured and classified. Appropriate protection is made against underflow exceptions.

$$Color(N) = Rnorm(N)/Gnorm(N)$$

if Color(N)<Green_Thr then Label_Pixel_Green if Color(N)<Brown_Thr then Label_Pixel_Brown 8. The Green, Brown, and Opaque labelings are stored as outputs in the Actuator Map.
9. The color image circular output pointer is advanced to discard the oldest row of color pixels.
10. The actuator circular input pointer is advanced to indicate the successful addition of a new row of labeled pixels.
11. Go back to step one, unconditionally.

The following table is a printout of a segment of a Color(N) array. The elements were sampled as a brown cullet fragment passed through the sensor. The number The shape and size of the brown cullet particle are visible as an oblong blob with ragged edges.

The following table is a printout of the Actuation(N) array and contains the same brown cullet image in the previous table. The number at the left of each row (382 ... 401) is the same time-stamp reference in the previous table. Individual values are shown as either "1" or "0", with each zero corresponding to no actuation and each one corresponding to an active actuation.

| | | | | | | | | | | | | | | | |
|---|---|---|---|---|---|---|---|---|---|---|---|---|---|---|---|
| 382 | 0 | 0 | 0 | 0 | 0 | 0 | 0 | 0 | 0 | 0 | 0 | 0 | 0 | 0 | 0 |
| 383 | 0 | 0 | 0 | 0 | 0 | 0 | 0 | 0 | 0 | 0 | 0 | 0 | 0 | 0 | 0 |
| 384 | 0 | 0 | 0 | 0 | 0 | 0 | 1 | 0 | 0 | 0 | 0 | 0 | 0 | 0 | 0 |
| 385 | 0 | 0 | 0 | 0 | 0 | 1 | 1 | 0 | 0 | 0 | 0 | 0 | 0 | 0 | 0 |
| 386 | 0 | 0 | 0 | 0 | 1 | 1 | 1 | 0 | 0 | 0 | 0 | 0 | 0 | 0 | 0 |
| 387 | 0 | 0 | 0 | 0 | 0 | 1 | 1 | 1 | 0 | 0 | 0 | 0 | 0 | 0 | 0 |
| 388 | 0 | 0 | 0 | 0 | 0 | 1 | 1 | 1 | 0 | 0 | 0 | 0 | 0 | 0 | 0 |
| 389 | 0 | 0 | 0 | 0 | 0 | 1 | 1 | 1 | 0 | 0 | 0 | 0 | 0 | 0 | 0 |
| 390 | 0 | 0 | 0 | 0 | 0 | 1 | 1 | 0 | 0 | 0 | 0 | 0 | 0 | 0 | 0 |
| 391 | 0 | 0 | 0 | 0 | 1 | 1 | 1 | 0 | 0 | 0 | 0 | 0 | 0 | 0 | 0 |
| 392 | 0 | 0 | 0 | 0 | 0 | 1 | 1 | 1 | 0 | 0 | 0 | 0 | 0 | 0 | 0 |
| 393 | 0 | 0 | 0 | 0 | 0 | 1 | 1 | 1 | 0 | 0 | 0 | 0 | 0 | 0 | 0 |
| 394 | 0 | 0 | 0 | 0 | 0 | 0 | 1 | 1 | 0 | 0 | 0 | 0 | 0 | 0 | 0 |
| 395 | 0 | 0 | 0 | 0 | 0 | 0 | 1 | 0 | 1 | 0 | 0 | 0 | 0 | 0 | 0 |
| 396 | 0 | 0 | 0 | 0 | 0 | 0 | 1 | 1 | 0 | 0 | 0 | 0 | 0 | 0 | 0 |
| 397 | 0 | 0 | 0 | 0 | 0 | 0 | 0 | 1 | 1 | 0 | 0 | 0 | 0 | 0 | 0 |
| 398 | 0 | 0 | 0 | 0 | 0 | 0 | 0 | 1 | 1 | 1 | 0 | 0 | 0 | 0 | 0 |
| 399 | 0 | 0 | 0 | 0 | 0 | 0 | 0 | 1 | 1 | 1 | 0 | 0 | 0 | 0 | 0 |
| 400 | 0 | 0 | 0 | 0 | 0 | 0 | 0 | 0 | 1 | 0 | 0 | 0 | 0 | 0 | 0 |
| 401 | 0 | 0 | 0 | 0 | 0 | 0 | 0 | 0 | 0 | 0 | 0 | 0 | 0 | 0 | 0 |

The final software segment is called the Ejection Task. It follows the logical flow described below.
1. The Ejection Task is periodically activated based on elapsed time.
2. Three rows of classification pixels are input from the actuator array. The proper row is identified by the actuator circular output pointer plus a fixed offset. The offset is correspond to the gravitational time delay between the sensing area and the actuation area.
3. Individual pixels are considered one at a time on the middle of the three rows. For each pixel in the row, steps 4 through 9 are repeated.

4. For each individual pixel, a local area neighborhood is developed which consists of the pixel itself and its eight immediate neighbors. These neighboring pixels are in the direction of north, south, east, west, NE, NW, SE, SW, with north pointing in the positive time axis. The eastern and western neighbors are eliminated from consideration at the extreme ends of the belt.
5. The values of the neighbors are summed.
6. If the central pixel is one and the neighboring sum is one or greater, then the corresponding air solenoid is actuated.
7. If the central pixel is one and the neighboring sum is zero, then the corresponding air solenoid is de-actuated.
8. If the central pixel is zero and the neighboring sum is three or more, then the corresponding air solenoid is actuated.
9. If the central pixel is zero and the neighboring sum is two or less, then the corresponding air solenoid is de-actuated.
10. After all pixels in the central row have been considered, the bottom (oldest) row is discarded by advancing a circular pointer. This task is performed identically for each bank or array of air solenoid actuators.
11. The task is suspended.

In this way, the particles are selected and classified based on their individual optical properties and ejected as desired.

The purified cullet streams are typically transported away from the sorting area on independent belt conveyors. At the end of the conveyors, they may be fed directly into remanufactories or they may be stockpiled to await use in the future. Impurities are disposed of separately as appropriate.

Figure 11:
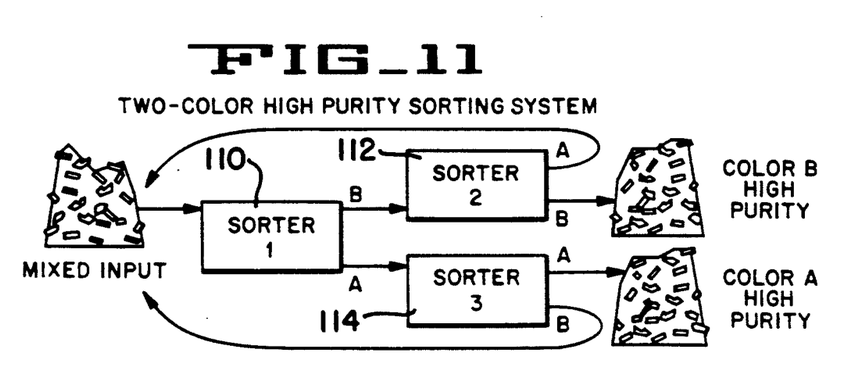
FIG. 11 illustrates another embodiment of a glass sorter.

FIG. 11 illustrates another configuration of the sorters. A first sorter 110 is set to separate material A from material B. Output B is fed into a second sorter 112, which also separates material A from material B. Output A from the second sorter 112 is fed back into the first sorter 110, while output B from the second sorter 112 is now twice purified output B. Output A from the first sorter 110 is fed to a third sorter 114. Output B from the third sorter is fed back to the first sorter 110, while output A from the third sorter is twice purified output A.

In addition to glass, other transparent materials such as plastics may be separated. In the specification and claims, transparent materials is defined as materials such as glass or plastic through which light is able to pass, which includes colored and translucent glass and plastic. If a soft plastic is being separated, the crushing means may provide a tearing or shredding action.

Figure 12:
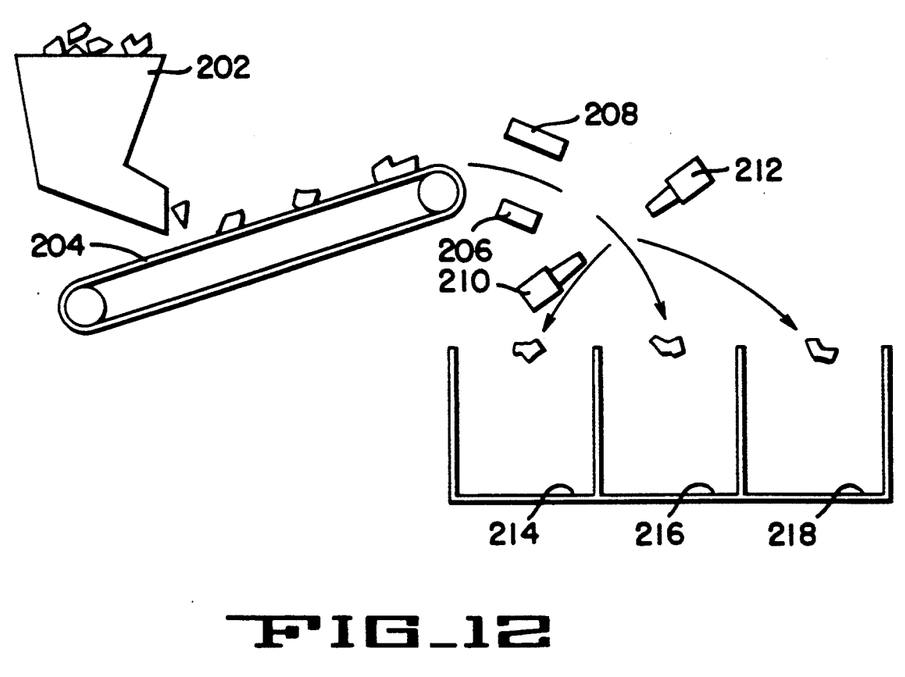
FIG. 12 illustrates another embodiment of a glass sorter.

FIG. 12 illustrates another embodiment of the invention. In this embodiment a loader 202 feeds crushed glass to a conveyor 204. The conveyor 204 trajects the crushed glass along a path first between a lamp array 206 and a sensor array 208 and then between a first array of actuators 210 and a second array of actuators 212. Along the trajectory is a first bin 214, a second bin 216, and a third bin 218. Light is transmitted from the lamp array 206 to the sensor array 208. Signals from the sensor array are processed and sent to a controller. The controller causes either an actuator from the first actuator array 210 to actuate or an actuator from the second actuator array 212 to actuate or no actuators to actuate. If an actuator from the first actuator array 210 actuates, crushed glass is blown by the air jet of the actuator into the third bin 218. If an actuator from the second actuator array 212 actuates, crushed glass is blown by the air jet of the actuator into the first bin 214. In no actuators are actuated, crushed glass falls into the second bin 216. Conveyors may be placed at the bottom of the bins 214, 216, 218 to convey the crushed glass to desired locations.

While preferred embodiments of the present invention have been shown and described herein, it will be appreciated that various changes and modifications may be made therein without departing from the spirit of the invention as defined by the scope of the appended claims.

What is claimed is:

1. An apparatus for the beneficiation of transparent material according to light transmitting properties of the transparent material, comprising:
   a control module;
   a first array of lamps, wherein the first array of lamps is electrically connected to the control module;
   a first array of sensors electrically connected to the control module and positioned opposed from the first array of lamps;
   a means for conveying the transparent material to a position above the first array of lamps and the first array of sensors and directing the transparent material between the first array of lamps and the first array of sensors; and
   an actuator means electrically connected to the control module for deflecting some of the transparent material dropped between the first array of lamps and the first array of sensors in response to the light transmitted from the first array of lamps through the transparent material to the first array of sensors.

2. An apparatus, as claimed in claim 1, wherein the actuator means, comprises at least one air jet.

3. An apparatus, as claimed in claim 2, wherein each lamp of the first array of lamps comprises a first light emitting a first frequency of light and a second light emitting a second frequency of light.

4. An apparatus, as claimed in claim 3, wherein the first light is an light emitting diode and the second light is a light emitting diode.

5. An apparatus, as claimed in claim 4, wherein the first frequency corresponds to the frequency of visible red light, and the second frequency corresponds to the frequency of visible green light.

6. An apparatus, as claimed in claim 4, wherein the transparent material are pieces of crushed lass, wherein the pieces are less than 3 inches in size.

7. An apparatus for the beneficiation of transparent material, comprising:
   a means for crushing the transparent material into pieces of transparent material; and
   a first sorter, comprising:
     a control module;
     a first array of lamps, wherein the first array of lamps is electrically connected to the control module;
     a first array of sensors electrically connected to the control module and positioned opposed from the first array of lamps;
     a means for conveying the pieces of transparent material to a position above the first array of lamps and the first array of sensors and directing the transparent material between the first array of lamps and the first array of sensors; and an actuator means electrically connected to the control module for deflecting some of the pieces of transparent material dropped between the first array of lamps and the first array of sensors in response to the light transmitted from the first array of lamps through the transparent material to the first array of sensors so that the actuator means provides deflected transparent material as a first output and undeflected material as a second output.

8. An apparatus, as claimed in claim 7, further comprising means for removing labels from the transparent material.

9. An apparatus, as claimed in claim 8, wherein the means for crushing crushes the transparent material to pieces of transparent material less than 3 inches in size.

10. An apparatus, as claimed in claim 7, further comprising a second sorter, comprising:
- a control module;
- a first array of lamps, wherein the first array of lamps is electrically connected to the control module;
- a first array of sensors electrically connected to the control module of the second sorter and positioned opposed from the first array of lamps of the second sorter;
- a means for conveying the pieces of transparent material from the first sorter to a position above the first array of lamps of the second sorter and the first array of sensors of the second sorter and directing the transparent material between the first array of lamps of the second sorter and the first array of sensors of the second sorter; and
- an actuator means electrically connected to the control module of the second sorter for deflecting some of the transparent material dropped between the first array of lamps of the second sorter and the first array of sensors of the second sorter so that the actuator means of the second sorter provides deflected transparent material as a first output and undeflected material as a second output 11. An apparatus, as claimed in claim 10, wherein the actuator means for the first sorter and the second sorter, comprises air jets.

12. An apparatus, as claimed in claim 11, wherein each lamp of the first array of lamps of the first sorter and the second sorter comprises a first light emitting a first frequency of light and a second light emitting a second frequency of light.

13. An apparatus, as claimed in claim 12, wherein the first light is an light emitting diode and the second light is a light emitting diode.

14. An apparatus, as claimed in claim 13, wherein the first frequency corresponds to the frequency of visible red light, and the second frequency corresponds to the frequency of visible green light.

15. A method of separating transparent material according to the light transmitting properties of the transparent material, comprising the steps of:
- passing the transparent material between a first array of lamps and a first array of sensors;
- transmitting light at a first frequency from the first array of lamps through the transparent material to the first array of sensors at a first time;
- transmitting light at a second frequency from the first array of lamps through the transparent material to the first array of sensors at a second time; and
- deflecting some of the transparent material according to the light received at the first array of sensors.

16. A method, as claimed in claim 15, further comprising the step of crushing the transparent material into pieces of transparent material less than 3 inches in size.

17. A method, as claimed in claim 16, further comprising the step of delabling the pieces of transparent material.

* * * * *